(12) United States Patent
Wolff et al.

(10) Patent No.: US 6,555,131 B1
(45) Date of Patent: Apr. 29, 2003

(54) THERAPEUTICAL SYSTEM FOR TRANSDERMAL DELIVERY OF LEVONORGESTREL

(75) Inventors: Hans-Michael Wolff, Monheim (DE); Christoph Arth, Dusseldorf (DE)

(73) Assignee: Schwarz Pharma AG, Monheim (DE)

( * ) Notice: Subject to any disclaimer, the term of this patent is extended or adjusted under 35 U.S.C. 154(b) by 0 days.

(21) Appl. No.: 09/462,009

(22) PCT Filed: Jul. 2, 1998

(86) PCT No.: PCT/EP01/94079

§ 371 (c)(1),
(2), (4) Date: Mar. 9, 2000

(87) PCT Pub. No.: WO99/01109

PCT Pub. Date: Jan. 14, 1999

(30) Foreign Application Priority Data

Jul. 4, 1997 (DE) .......................................... 197 28 516

(51) Int. Cl.[7] .......................... A61F 13/00; A61L 15/16; A61K 9/14
(52) U.S. Cl. ....................... 424/449; 424/484; 424/487; 424/448; 424/443
(58) Field of Search ................................. 424/449, 448, 424/443

(56) References Cited

U.S. PATENT DOCUMENTS

| 5,730,999 A | * | 3/1998 | Lehmann et al. |
| 5,762,956 A | * | 6/1998 | Chien et al. |
| 5,985,311 A | * | 11/1999 | Cordes et al. ............... 424/428 |
| 6,063,399 A | * | 5/2000 | Assmus et al. |
| 6,165,499 A | * | 12/2000 | Kleinsorgen et al. |

FOREIGN PATENT DOCUMENTS

| DE | 3823070 | 2/1990 | ........... A61L/15/22 |
| EP | 563 507 | * 10/1993 | ............ A61K/9/70 |
| EP | 0 848 960 | 6/1998 | ........... A61L/15/58 |

* cited by examiner

Primary Examiner—Carlos Azpuru
Assistant Examiner—Isis Ghali
(74) Attorney, Agent, or Firm—Marshall, Gerstein & Borun

(57) ABSTRACT

A stable therapeutical transdermal system for the transcutaneous delivery of levonorgestrel, alone or together with other sex steroid hormones, over a long time period is disclosed. A method of producing the transdermal system that avoids the use of solvents and avoids degradation of the steroid hormones also is disclosed.

15 Claims, No Drawings

THERAPEUTICAL SYSTEM FOR TRANSDERMAL DELIVERY OF LEVONORGESTREL

The present invention concerns a Transdermal Therapeutic System (TTS) for the administration of levonorgestrel alone or with other steroid sex hormones through the skin over a longer period of time, as well as a method for its production without the use of solvents, the method being especially protective for the active ingredient.

The bioavailability of orally administered active ingredients is frequently unsatisfactory. Metabolization of many active ingredients in the liver can lead during the first passage through the liver to undesirable concentration relationships, toxic by-products and to the reduction of the activity and even to loss of activity. In comparison to oral administration, transdermal administration of active ingredients has various advantages. The introduction of the active ingredient can be controlled better over a longer period of time as a result of which high fluctuations in blood level are avoided. In addition, the required therapeutic effective dose can mostly be reduced significantly. In addition, patients frequently prefer a plaster to tablets, which must be taken once or several times daily.

In the past, in order to overcome the disadvantages of nontransdermal administration of active ingredients mentioned above, a number of transdermal therapeutic systems (TTS) with different structure were proposed for various active ingredients for the therapy of different diseases.

Thus, the technical documents given below describe a broad variety of systemically or locally reacting active ingredients, their parenteral administration either based on dose-controlled or generally releasing systems. For example, these are: U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,573,995; 4,588,580; 4,645,502; 4,702,282; 4,788,062; 4,816,258; 4,849,226; 4,908,027; 4,943,435 and 5,004,610.

In the late sixties of this century, it was assumed originally theoretically that all active ingredients with short half-life but high activity and good penetration of the skin would be suitable for safe and effective administration via a TTS. These early expectations regarding the possibilities of transdermal administration of active ingredients by TTS could, however, not be fulfilled. The reason for this is mainly that the skin is equipped naturally with an inassessable variety of properties in order to maintain its function as an intact barrier to the penetration of substances that are foreign to the body. (See in this regard: Transdermal Drug Delivery: Problems and Possibilities, B. M. Knepp et al., CRC Critical Review and Therapeutic Drug Carrier Systems, Vol. 4, Issue 1 (1987).)

Therefore, transdermal administration is available only for those few active ingredients which have a suitable combination of many favorable characteristics. For a given active ingredient, all other required characteristics that permit safe and effective transdermal administration cannot be predicted, either theoretically or practically.

The requirements for an active ingredient suitable for transdermal administration are the following:

permeability through the skin, no adverse influence on the adhesiveness of the plaster by the active ingredient, avoidance of skin irritations, avoidance of allergic reactions, favorable pharmacokinetic properties, favorable pharmacodynamic properties, relatively broad therapeutic window, metabolic properties which are consistent with the therapeutic application with continuous administration.

Undoubtedly, the above list of requirements is not exhaustive. In order for having an active ingredient available for transdermal application, the "correct" combination of all these requirements is desirable. What was said above for active ingredient applies similarly to the TTS composition containing the particular ingredient and to its structure.

Usually, transdermal therapeutic systems (TTS) are plasters which are equipped with an impermeable cover layer, a removable protective layer and a matrix which contains the active ingredient or a reservoir. With semipermeable membrane, which contains the active ingredient. In the first case, they are called matrix plasters and in the second case, they are called membrane systems.

For the cover layer, usually films made of polyester, polypropylene, polyethylene, polyurethane, etc., are used which can also be metallized or pigmented.

For the removable protective layer, among others, films made of polyester, polypropylene or even paper with silicone and/or polyethylene coating come into consideration.

For the active-ingredient-containing matrices which are usually used pharmaceutically or medically, polymer materials based on polyacrylate, silicone, polyisobutylene, butyl rubber, styrene/butadiene copolymer or styrene/isoprene copolymer are used.

The membranes used in the membrane systems can be microporous or semipermeable and are usually based on an inert polymer, especially polypropylene, polyvinyl acetate or silicone.

While the active-ingredient matrix compositions can be self-adhesive, depending on the active ingredient used, one can also have active-ingredient containing matrices, which are not self-adhesive, so that, as a consequence of this, the plaster or TTS must have an overtape in its structure.

In order to ensure the required flux rate of the active ingredient, frequently skin penetration enhancers are necessary as additives, such as aliphatic, cycloaliphatic and/or aromatic-aliphatic alcohols, which can be monovalent or polyvalent and may have up to 8 C-atoms, including an alcohol/water mixture, a saturated and/or unsaturated fatty alcohol with 8 to 18 carbon atoms, a saturated and/or unsaturated fatty acid with 8 to 18 carbon atoms and/or their esters, as well as vitamins.

Furthermore, frequently stabilizers such as polyvinylpyrrolidone, α-tocopherol succinate, propyl gallate, methionine, cysteine and/or cysteine-hydrochloride are added to the active-ingredient-containing matrix.

As the above discussion shows, numerous TTS structures and the materials used for them are known. In any case, there are many interacting requirements to be considered when a drug is to satisfy medical requirements in the form of a TTS.

The following problems are to be considered fundamentally in the development of active-ingredient-containing TTS:

1. In order to achieve the therapeutically necessary penetration rates of the active ingredient through the skin, mostly it is required to have a high load of active ingredient in the polymer matrix. After the end of application, the active ingredient remaining in the TTS is not used therapeutically and is disposed with the plaster. However, this is undesirable, especially in the case of highly active and expensive active ingredients for reasons of environmental protection and costs.

2. The polymer matrix which is loaded with the active ingredient and optionally additionally with skin penetration enhancers is not stable physically upon long storage. Especially, recrystallization of the active ingredient may occur, which leads to an uncontrollable decrease of the release capacity of the TTS for the active ingredient.
3. High load of the polymer carrier with active ingredient and/or skin penetration enhancers makes the adjustment of optimum adhesive properties of the transdermal system difficult in the case of self-adhesive polymer films.
4. The resorption rate of the active ingredient decreases during application over several days in an unacceptable manner, so that additional control layers and/or components are necessary.
5. If the active-ingredient-loaded layers are made of organic solutions, the problem of remaining solvent residues in the active-ingredient-containing layer occurs after the drying process. Additionally, there is a danger of undesirable evaporation of volatile additives during manufacture. Since, for reasons of physical stability and skin compatibility of the system, as a rule, an attempt is made to have our system completely free from solvent, and, optionally, the reservoir therefore must be built up in several layers. This again leads to an increase of manufacturing costs.

Therefore, the problems described above require a number of embodiments of Transdermal Therapeutic Systems, which are reflected in the state of the art in this field.

A more recent review on this is given, for example, in U.S. Pat. No. 5,662,926 (Wick et al., 1997). This document describes transdermal systems which contain a monolithic thermo-plastic polymer film in which an active ingredient, preferably nicotine, is distributed homogeneously, as well as a method for solvent-free production of this active-ingredient-containing layer by mixing the active ingredient with the polymeric carrier material in the polymer melt, at temperatures from 170° C. to 200° C. In order to attach the active-ingredient-containing matrix film on the skin, there is an additional contact adhesive film which is applied onto the active ingredient matrix, and, if necessary, there is an additional plaster which has a larger area which is applied on the side of the matrix away from the skin onto the active-ingredient-containing polymer film.

Special pharmaceutical technical problems are to be solved in the development of estrogen plasters which must be applied for the treatment of climacteric complaints. The application should occur only once or twice per week. Increasing attention was received in this connection by the so-called 7-day plasters for reasons of cost and patient compliance in this indication. Cost aspects are of special importance here because many steroid sex hormones which are provided for continued therapy are highly costly drugs. In addition, when hormones are administered, for medical reasons, frequently a combination therapy is desired.

Thus, the natural estrogen—17β-estradiol—is usually used for the treatment of climacteric complaints, either continuously or sequentially together with a gestagen.

An adequately known form of execution of such TTS are monolithic active ingredient plasters, which make controlled release of the active components possible from a thin adhesive layer. However, in practice, the development of such active ingredient plasters with steroid sex hormones, especially when used over several days, encounter one or several of the difficulties outlined below, which frequently can be solved only by expensive measures and which increase the development and/or manufacturing costs. These are essentially the following problems:

1. The steroid sex hormone is released from the adhesive films at a relatively low rate per unit time through the skin, with the consequence that relatively large plasters must be applied in order to build up the therapeutically necessary hormone level in the blood over a long period of time and/or the so-called penetration accelerator must be administered together with the active ingredient(s) in order to achieve the required transepidermal transport rate.
2. The steroid sex hormone is physically unstable in the self-adhesive film, depending on the storage conditions, that is, there is especially the danger of recrystallization of an active ingredient during storage, which is related to uncontrollable decrease of the active ingredient release capacity.
3. The active ingredient resorption rate drops during use over several days in an unacceptable manner, so that additional control layers or control components are necessary.
4. High loading with active ingredient and penetration accelerators makes the optimum adjustment of the adhesive properties of the TTS difficult during development.

For example, cold flow of the self-adhesive reservoir layer represents special problems which, in human application, can lead to leakage of the active-ingredient-containing mass beyond the edge of the plaster and thus to dirty edges. Furthermore, partial or complete separation of the TTS, caused by the action of moisture (for example, during taking a shower, swimming, heavy sweating) and/or due to high shear stresses as a result of muscular or skin movements, can be observed at the skin/plaster boundary.

5. Reservoir layers for the transdermal application are frequently prepared from solutions, so that the problem of remaining solvent residues in the active-ingredient-containing layer after the drying process and optionally the related vaporization and/or undesirable evaporation of volatile additives during the manufacture occurs. In order to achieve complete absence of solvent, which should be strived for as a rule for reasons of physical stability and skin compatibility of the system, the reservoir should optionally be built from several layers, but this would lead to making the manufacture more expensive.

Regarding the transdermal application of estrogens and/or gestagens and/or androgens with the aid of monolithic systems, in which the active ingredient or ingredients are incorporated into a self-adhesive matrix, according to the state of the art—among others, because of their relatively good solvent properties for this group of active ingredients—preferably adhesives based on acrylate copolymers are used without (EP 0 416 8412, WO 93/10772) or with (WO 96/08255, DE 44 05 898) the addition of penetration-promoting, crystallization-inhibiting (WO 95/09618, WO 93/08795), active-ingredient solubility-enhancing (DE OS 44 05 898) and water-binding (DE 39 33 460) substances.

As a rule, the described formulations require the use of organic solvents, which must be removed again quantitatively during manufacture. Also, in spite of the relatively simple structure of monolithic TTS, the usual pharmaceutical quality requirements regarding adhesive properties, reproducibility of the active ingredient release and storage stability can only be provided with high technical expenditure in the development and production because of the difficulties described above. Frequently, large-area plasters must be applied, especially for the administration of gestagens, in order to maintain the required active ingredient level in the blood over several days of application, as a result of which, first of all, the use properties and the related patient compliance become worse and, on the other hand, the cost of the preparation is increased further.

Furthermore, monolithic systems with sex steroids based on polystyrene block copolymers as carrier materials are known from the literature, the use of which permits in principle the production of self-adhesive active ingredient reservoirs from the melt without the use of organic solvents. Thus, in WO 94/26257, steroid-containing adhesives are described, which contain esters of colophonium and in which the manufacture of estradiol- and/or levonorgestrel-containing adhesive matrix can be done by melting and intensive kneading at high temperature over a long period of time. Transdermal Therapeutic Systems which are produced in this way have the disadvantage that the active ingredient (s) and/or pharmaceutical additives partially decompose under the conditions of the manufacturing process, that the adhesive properties and/or skin compatibility of the plaster are insufficient over several days and—especially for the gestagen component—the attainable plasma concentrations are therapeutically insufficient.

Furthermore, active ingredient plasters are known from EP 0 186 019 in which swellable polymers are added to a rubber adhesive mass in water and from which estradiol can be liberated and in some individual cases, manufacture according to the hot-melt method is possible. With these formulations, it is still difficult to have sufficient amounts of steroid sex hormones contained in the plaster matrix in solution and to release these over a long period of time at an approximately constant rate through the skin.

Furthermore, formulations are known from DE 44 29 667 for the transepidermal release of estradiol, which are produced without the use of organic solvents by melting the components of the formulation with glycerol being added as protection against the precipitation of the estradiol hemihydrate during storage. The adhesive formulations, named in the Description and in the Examples, based on polystyrene block copolymers, correspond to the state of the art, that is, the active ingredient uptake and release capacity of TTS of this type are generally too low for application of the hormone plaster over several days, in general, especially in the case of gestagens and androgens.

In addition to the monolithic system, the multilayer matrix and reservoir systems are also adequately known from the literature, in which the active ingredient reservoir, adhesive layer and/or release-control layers are separated from one another functionally and/or spatially. EP 0 285 563 describes a TTS for the combined application of estrogens and gestagens.

Here, the active ingredient reservoir contains ethanol as solvent and release-control agent for the active components. Furthermore, a membrane also participates in the control of the release of the steroidal hormones, being located between the reservoir and the separately arranged adhesive layer. The possible duration of application of such TTS depends, among others, greatly on the ethanol content in the reservoir (J. A. Simon et al. (1991), Fertility and Sterility, 56: 1029–1033), which, during application, decreases continuously during resorption and thus limits the functional lifetime of the system. Since, in addition to the active ingredient, another component which increases resorption is also released at a relatively high rate, depending on the environmental storage and application conditions, there is a risk of physical instability, decreasing adhesive force and/or local skin irritations.

A so-called "enhanced" system, in which, besides the active ingredients penetration accelerators are released on the skin and which contain separate reservoir, control and adhesive layers, is known and from the state of the art, again for the transepidermal application of testosterone (U.S. Pat. No. 5,152,997).

This TTS has the advantage for the patient that it does not have to be adhered to the relatively permeable scrotal skin, which is the case otherwise, due to the low absorption of the active ingredient of testosterone plasters without penetration aid (for example, according to DE OS 35 23 065). An application of such "enhanced" systems, however, is related to a higher risk of local skin irritation when used for more than 24 hours, caused by the additives that control the skin permeation of the testosterone. Especially, in the case of unfavorable application conditions (perspiring, strong skin movements, showers), problems occur relating to the adhesion properties.

Finally, in the development of transdermal systems, polymers based on acrylic acid esters and methacrylic acid esters are of special interest because of their relatively good ability to take up and release a number of active ingredients. In order to avoid the use of solvents in the manufacture of matrix systems based on poly(meth)acrylate, DE 4310012 describes a dermal therapeutic system in which one or several layers are made of mixtures of poly(meth)acrylates and are produced from the melt and the first mixing component consists of (meth)acrylic polymers which contain functional groups, the second mixing component controls the flow behavior and contains only insignificant amounts of functional groups. The composite systems with poly(meth) acrylates with functional groups are supposed to make it possible to have controlled release of the active ingredient(s) on or through the skin and facilitate simple manufacture. The advantages in the manufacture in comparison to solvent-based methods, however, has in these systems a number of disadvantages according to experience and these are caused by the following:

1. Longer-lasting thermal exposure of all TTS components during (1) manufacture of the polymer melt, (2) homogeneous incorporation of the active ingredient or ingredients and/or (3) coating of the hot active-ingredient-containing mass onto suitable carrier materials, with an increased risk of degradation or decomposition reactions in the polymer melt and/or during storage of the active-ingredient-containing polymer films.
2. Difficulties in the optimization of the cohesion/ adhesion balance of the poly(meth)acrylate-containing layer, since crosslinking of the acrylate copolymer with covalent bonds during manufacture of the active-ingredient-containing polymer matrix in the melt is not possible, in combination with problems that can arise because of cold flow of the polymer mass during application on the skin and/or during storage.
3. Strong bonding of the active ingredient/steroid hormones, especially of 17β-estradiol in the polymer matrix by poly(meth)acrylates with a high content of free amino groups, as a result of which the flux rates of the sex steroid are reduced in comparison to poly(meth) acrylate matrices without free amino groups—at the same loading with active ingredient—(see FIG. 1, Comparison Example).

As the above list shows, many plaster constructions and materials used for these are known. Similarly, today there is still a great demand for many active ingredients that are incorporated into Transdermal Therapeutic Systems to have a TTS available, which make it possible to provide the therapeutically required release of the active ingredient without the construction being expensive and in which, overall, the components are in an optimal relationship.

This also applies to the active ingredient levonorgestrel, when it is to be administered transcutaneously.

Therefore, the task of the invention is to avoid the disadvantages of TTS with sex steroids described above and to provide a TTS for transepidermal administration of levonorgestrel alone or with other sex steroids, with good adhesive properties, and which is simple to construct, compatible with the skin and is physically and chemically stable over a long duration of storage and application and which a) releases on and through the skin as much active ingredient as possible, b) is free from solvent and c) in which the active ingredient or ingredients used experience as little thermal exposure as possible.

In order to solve this task, a TTS, which contains the active ingredient levonorgestrel alone or with other sex steroids and a method for its manufacture without the use of solvents, is made available, the special composition of which, corresponding to the Patent Claims, surprisingly can fulfill the tasks described above.

The Transdermal Therapeutic System (TTS) according to the invention contains a steroid-hormone-containing, especially levonorgestrel-containing matrix composition in the form of a layer in which the matrix composition contains ammonium-group-containing (meth)acrylate copolymers which are extruded in the melt up to 200° C., and at least one plasticizer and a fatty acid ester, and, if desired, polyethylene glycol, as well as at least 2 weight % of each steroid hormone present in the matrix composition, incorporated without premelting and has a cover layer toward the outside. The TTS according to the invention does not require any additional adhesive layer for attachment to the skin. The matrix layer contains the active ingredient and also attaches the TTS to the skin. The release rates that can be achieved with the TTS according to the invention are so high that the application time can be increased in comparison to the plaster systems known from the state of the art, without increasing the application area (see FIG. 1).

In the development of the TTS according to the invention, surprisingly, it was possible to optimize advantageously the cohesion/adhesion properties of the TTS on the one hand and the solubility, rate of dissolution and release behavior of the active ingredient on the other hand. The increased liberation of the active ingredient, levonorgestrel, based on the combination according to the invention of ammonium-group-containing (meth)acrylate copolymers with triethyl citrate and the active ingredient, levonorgestrel, is especially surprising. Furthermore, regarding the TTS according to the invention, it is surprising that (1) in contrast to the state of the art, high active ingredient concentrations in the polymer matrix at the same time provides a sufficient physical stability of the system during long-term storage and that (2) the introduction of separate separating layers or membranes between the active-ingredient-containing layer and the layer without active ingredient can be omitted.

Surprisingly, in the type of TTS according to the present invention, the outstanding flux properties of the active-ingredient-containing matrix are combined with outstanding adhesive properties. Immediately after adhering the TTS, an intimate contact is established between the active ingredient matrix and the skin. If, according to one of the embodiments of the present invention, crosslinkable adhesive layers are laminated directly onto the active ingredient layer as an attachment aid, the self-adhering TTS obtained in this way, consisting of covering layer, active ingredient layer and adhesive layer also show surprisingly high steroid release rate over long time periods of application.

According to another embodiment of the invention, the TTS consisting of covering layer and active ingredient layer, can be surrounded by a larger, active-ingredient-free skin plaster for attachment to the site of application, with the exception of its release area on the skin. In this embodiment, the protruding width of this attachment aid can be very narrow because of the outstanding adhesive properties of the active-ingredient-containing matrix layer. Advantageously, this attachment aid surrounds the TTS on the edge with 2–4 mm.

It is especially advantageous according to the invention that the TTS contains the particular active ingredient in a state which experiences minimum thermal exposure. It is added without melting to the matrix composition that was heated by melt-extrusion.

The embodiment according to the invention, in which the steroid-hormone-containing matrix composition is a solid solution, is advantageous.

The steroid-hormone-containing matrix composition according to the invention contains citric acid triester as plasticizer as well as preferably an ester of oleic acid or nonanoic acid as fatty acid ester.

Embodiments of the invention include TTS, the estrogens or gestagens alone or in combination.

Advantageously, the carrier film used for the TTS has a metal vapor or oxide layer on the matrix side.

In the sense of the invention the following terms and/or words are defined as given below:

a) "solvent-free": no solvent is used for the manufacture of the polymer matrices which solvent would have to be removed again largely during the manufacturing process, as it is done in the "solvent-based" method.

b) "longer application time period": The TTS can be applied to the skin for therapeutic application for up to 7 days.

c) "solid solution": the pharmaceutical active ingredient is present in the plaster matrix in the molecularly dispersed form.

d) "transepidermal": same meaning and function as transcutaneous.

e) "thermally minimally exposed active ingredient": the active ingredient is added without melting to the matrix composition which was heated by melt-extrusion, which is then cooled after the addition of the active ingredient.

The method of the production of the TTS according to the invention is characterized by the fact that a coatable steroid-hormone-containing matrix composition is produced by melt-extrusion, in which the active components are weighed and incorporated continuously without premelting into the hot polymer melt heated up to 200° C., the hot active-ingredient-containing polymer melt is then coated directly onto a separable protective layer (=substrate) to a thickness of 0.02 to 0.4 mm and then the obtained 2-layer laminate is covered with a cover layer.

If desired, an active ingredient-free adhesive film made of a crosslinked acrylate copolymer can be laminated directly onto the active-ingredient-containing polymer matrix. The TTS according to the invention are provided with a protective film which is removed before application of the preparation onto the skin.

An essential advantage of the method according to the invention consists in the fact that the active ingredient reservoir (I) is produced without using any organic solvents, and (II) the preparation of the active-ingredient-containing matrix composition and its further processing to an active-ingredient-containing layer can be done in a continuous and cost-saving process step: the processing times can be reduced to a few minutes and thus at the same time the danger of decomposition reactions in the active-ingredient-containing polymer melt can be reduced to a minimum. Surprisingly, it was found that the complete dissolution of the sex steroid(s) in the polymer melt is provided in spite of the short process times under the processing conditions which are explained further in the examples.

Furthermore, as a result of the continuous manufacture of the steroid-hormone-containing polymer mass, scaling-up problems are avoided. That is, in order to increase the batch size or charge size, no changes are necessary to larger production installations or the manufacture of the active-ingredient-containing polymer melt or of the laminate, which usually requires time-consuming and expensive installation, qualification and validation work as well as also changes in the formulation.

The invention will be explained below with the aid of Examples:

COMBINATION-TTS WITH LEVONORGESTREL AND ESTRADIOL

1. EXAMPLES 1 TO 4

A two-extruder with the screws running in the same direction, equipped with two metering devices, is continuously charged in two successive process zones with a homogeneous solid mixture A as well as with a liquid mixture B. (See Table 1 for the composition of mixtures A and B.) The batch is melt-extruded at a total throughput of 1 kg/h at a temperature of 150° C., introducing mixture A from metering device 1 into the first process part at a rate of 690 g/h and introducing mixture B from metering device 2 into the second process part at a rate of 310 g/h.

The obtained hot polymer melt is applied onto an approximately 100 μm thick silicone-coated polyester film (=protective film) as a layer, so that the weight of application of the polymer mass is approximately 80 g per m². The two-layer material, consisting of the protective film and the matrix composition is cooled to room temperature and then covered with an approximately 20 μm thick polyester film (=carrier film) and the three-layer laminate thus obtained is stamped into pieces with an area of 16 cm².

The resulting combination-TTS contain the amounts of active ingredient given in Table 2.

TABLE 1

Composition of the TTS (Examples 1 to 4)

| component | Example 1 content in weight % | Example 2 content in weight % | Example 3 content in weight % | Example 4 content in weight % |
| --- | --- | --- | --- | --- |
| mixture A | | | | |
| levonorgestrel | 2.9 | 7.0 | 7.0 | 2.9 |
| estradiol | 4.3 | 3.6 | 3.6 | / |
| Eudragit RL 100 | 30.9 | / | / | / |
| Eudragit RS 100 | / | 44.7 | 44.7 | 97.1 |
| Eudragit E 100 | 61.9 | 44.7 | 44.7 | / |
| mixture B | | | | |
| triethyl citrate | 67.7 | / | / | / |
| tributyl citrate | / | 51.0 | 51.0 | 100.0 |
| polyethylene glycol 400 | 32.3 | 32.6 | 32.6 | / |
| oleic acid ethyl ester | / | 16.4 | / | / |
| nonanoic acid ethyl ester | / | / | 16.4 | / |

II. IN-VITRO INVESTIGATIONS

Skin-permeation measurement in vitro

In order to evaluate the release of the active ingredient in vitro, a TTS with a stamped-out area of 5 cm² is secured in a modified Franz diffusion cell on a hairless mouse skin preparation. Immediately afterward, the cell is filled with distilled water as release medium, without any air bubbles, and is thermostated to 32±0.5° C.

At the sampling times, the release medium is replaced by fresh water thermostated to 32±0.5° C.

The active ingredient content in the removed release medium is determined using high-performance liquid chromatography. The results of the investigations are presented in Table 2 for Examples 1 to 4 and a commercial matrix combination plaster with a declared release rate of 50 μg of estradiol and 20 μg of levonorgestrel per day. As comparison of the flux rates in Table 2 shows, clearly more levonorgestrel is released through the skin from the TTS according to the invention than from the reference plaster. Even in Example 4, which does not contain any penetration mediator and has a lower active ingredient charge in comparison to Examples 1 to 3, the flux rate after 24 hours is comparatively still higher than for the commercial preparation, which contains a penetration mediator. In the TTS with higher estradiol concentration (Examples 2 and 3), the estradiol flux rates are also above the values measured for the commercial preparation.

TABLE 2

(1) levonorgestrel (LN) content and flux rates through excised mouse skin

| TTS test preparation | LN content weight % based on the polymer matrix | cumulative LN flux rates ($\mu g/cm^2$), mean values, n = 3 after 24 h | after 48 h |
| --- | --- | --- | --- |
| Example 1 | 2.69 | 13.47 | 27.40 |
| Example 2 | 2.44 | 16.89 | 31.11 |
| Example 3 | 2.47 | 13.02 | 25.43 |
| Example 4 | 1.70 | 6.50 | — |
| commercial preparation (matrix plaster) | 0.84 | 6.15 | 11.48 |

TABLE 2-continued (2) Estradiol (E2)-content and flux rates through excised mouse skin

| TTS test preparation | E2 content weight % based on the polymer matrix | cumulative E2 flux rates ($\mu g/cm^2$), mean values, n = 3 | |
| --- | --- | --- | --- |
| | | after 24 h | after 48 h |
| Example 1 | 1.85 | 7.77 | 15.92 |
| Example 2 | 4.94 | 28.57 | 54.14 |
| Example 3 | 4.98 | 21.49 | 42.56 |
| commercial preparation (matrix plaster) | 2.23 | 16.70 | 31.64 |

Explanations:
— = not determined

What is claimed is:

1. A transdermal therapeutic system for transcutaneous administration of levonorgestrel and additional optional sex steroids over a period of up to seven days, wherein the system comprises a layer of a steroid-containing matrix composition disposed on a carrier film, said matrix composition comprising a solid solution of (a) a copolymer of ethyl acrylate and methyl methacrylate containing about 5% trimethylammonium ethyl methacrylate chloride as the sole (meth)acrylate copolymer, (b) about 20 weight percent to about 30 weight percent of one or more plasticizers selected from the group consisting of esters of weak organic acids, (c) an optional fatty acid ester, and (d) at least 2 weight percent of levonorgestrel and each optional sex steroid distributed in the matrix composition as a molecular dispersion, wherein the system contains at least one sex steroid hormone which had minimum thermal exposure, and wherein the system is free of an adhesive layer.

2. A transdermal therapeutic system for the transcutaneous administration of levonorgestrel over a period of up to seven days, wherein the system comprises a layer form of a levonorgestrel-containing matrix composition disposed on a carrier film, said matrix composition comprising (a) a copolymer of ethyl acrylate and methyl methacrylate containing about 5% trimethylammonium ethyl methacrylate chloride as the sole (meth)acrylate copolymer, (b) about 20 weight percent to about 30 weight percent of at least one plasticizer selected from the group consisting of esters of weak organic acids, (c) an optional fatty acid ester, and (d) at least 2 weight percent of levonorgestrel distributed in the matrix composition in a molecularly dispersed form, wherein the levonorgestrel had minimum thermal exposure, and wherein the system is free of an adhesive layer.

3. The system of claims 1 and 2 wherein, with the exception of a release surface on the skin, the system is surrounded by a larger active-ingredient-free skin plaster for attachment at an application site.

4. The system of claims 1 and 2 wherein the steroid-hormone-containing matrix contains citric acid triester as the plasticizer.

5. The system of claims 1 and 2 wherein the steroid-hormone-containing matrix contains an ester of oleic acid or nonanoic acid as the fatty acid ester.

6. The system of claims 1 and 2 wherein the system contains estrogens or gestagens alone or in combination.

7. The system of claims 1 and 2 wherein the carrier film has a metal vapor or oxide coating on the matrix side.

8. The system of claims 1 and 2 wherein the system is free of a rate-controlling polymer layer for delivery of the sex steroids.

9. A method of producing a transdermal therapeutic system of claim 1 or 2 comprising:

(a) forming a solid mixture comprising (i) levonorgestrel and additional optional sex steroids and (ii) a copolymer of ethyl acrylate and methyl methacrylate containing about 5% trimethylammonium ethyl methacrylate chloride as the sole (meth)acrylate copolymer;

(b) forming a liquid mixture comprising at least one plasticizer and an optional fatty acid ester;

(c) continuously melt coextruding the solid mixture of step (a) and the liquid mixture of step (b) at a temperature sufficiently low and for a time sufficiently short to maintain the levonorgestrel and optional sex steroids in a nonmolten form to form a matrix composition, and continuously applying the matrix composition onto a protective film to a thickness of 0.02 to 4 mm; and (d) applying a carrier film on a surface of the matrix composition opposite from the protective film.

10. The method of claim 9 wherein a larger sex steroid-free plaster is applied to the transdermal therapeutic system to provide a cover layer for attaching the system to skin.

11. The method of claim 9 wherein the optional sex steroid is estradiol.

12. The method of claim 11 wherein the melt coextrusion temperature is about 150° C.

13. The method of claim 9 wherein the protective film comprises a silicone-coated polyester film.

14. The method of claim 9 wherein the carrier film comprises a polyester film.

15. A transdermal therapeutic system for the transcutaneous administration of levonorgestrel and additional optional sex steroids over a period of up to seven days, wherein the system comprises a layer form of a levonorgestrel-containing matrix composition disposed on a carrier film, said matrix composition consisting essentially of (a) a copolymer of ethyl acrylate and methyl methacrylate containing about 5% trimethylammonium ethyl methacrylate polymer as the sole (meth)acrylate copolymer, (b) about 20 weight percent to about 30 weight percent of at least one plasticizer selected from the group consisting of esters of weak organic acids, (c) an optional fatty acid ester, and (d) at least 2 weight percent of levonorgestrel distributed in the matrix composition in a molecularly dispersed form, wherein the levonorgestrel had minimum thermal exposure, and wherein the system is free of an adhesive layer, said system prepared by a method comprising:
(a) forming a solid mixture comprising the levonorgestrel, optional sex steroids, and the ethyl acrylate and methyl methacrylate copolymer;
(b) forming a liquid mixture comprising at least one plasticizer and an optional fatty acid ester;
(c) continuously melt coextruding the solid mixture of step (a) and the liquid mixture of step (b) at a temperature sufficiently low and for a time sufficiently short to maintain the levonorgestrel in a nonmolten form to form the matrix composition, and continuously applying the matrix composition onto a protective film to a thickness of 0.02 to 4 mm; and
(d) applying a carrier film on a surface of the matrix composition opposite from the protective film.

* * * * *